United States Patent
Rahim (12) 
(10) Patent No.: US 10,816,523 B2
(45) Date of Patent: Oct. 27, 2020

(54) MOLD ASSESSMENT BEHIND A SURFACE

(71) Applicant: AROMATIX, INC., Santa Clara, CA (US)

(72) Inventor: Chowdhury F. Rahim, Santa Clara, CA (US)

(73) Assignee: Aromatix, Inc., Santa Clara, CA (US)

(*) Notice: Subject to any disclaimer, the term of this patent is extended or adjusted under 35 U.S.C. 154(b) by 0 days.

(21) Appl. No.: 16/295,871

(22) Filed: Mar. 7, 2019

(65) Prior Publication Data

US 2020/0284772 A1 Sep. 10, 2020

(51) Int. Cl.
- *H04W 4/38* (2018.01)
- *G01N 33/00* (2006.01)
- *C12Q 1/24* (2006.01)

(52) U.S. Cl.
CPC ........... *G01N 33/004* (2013.01); *C12Q 1/24* (2013.01); *H04W 4/38* (2018.02)

(58) Field of Classification Search
CPC .................................................. G01N 33/004
See application file for complete search history.

(56) References Cited

U.S. PATENT DOCUMENTS

| | | | | |
|---|---|---|---|---|
| 5,476,001 A | * | 12/1995 | Hoetzel | G01N 27/419 73/23.31 |
| 8,056,394 B2 | * | 11/2011 | Frerichs | G01N 27/4143 73/25.01 |
| 2009/0272175 A1 | * | 11/2009 | Frerichs | G01N 27/4143 73/25.01 |
| 2015/0062885 A1 | * | 3/2015 | Martinez | F21L 4/02 362/184 |
| 2018/0149586 A1 | * | 5/2018 | Yokota | G01N 21/3504 |

\* cited by examiner

*Primary Examiner* — Qutbuddin Ghulamali
(74) *Attorney, Agent, or Firm* — Tyler Jeffs; Fabian VanCott (57) ABSTRACT

This document describes a method of determining an extent of mold behind a surface. The method includes moving a gas sensor lateral to the surface. The gas sensor includes an oscillating gas-interacting surface. The method includes measuring gas concentrations at multiple points along the surface. The method also includes displaying a heat map in a display. The heat map shows gas concentrations at multiple points along the surface.

14 Claims, 6 Drawing Sheets

MOLD ASSESSMENT BEHIND A SURFACE

BACKGROUND

Mold represents an established risk to health and is associated with respiratory disease and other chronic health issues. Water and mold damage represent an estimated 2.5 billion dollar cost in the United States per year. Estimates of health costs are also in the billions with black mold estimated to be responsible for about 20% of asthma and allergy cases. Some estimates of total economic impact, including indirect costs, run into the 100s of billions of dollars.

Mold may grow in areas of water damage, for example from flooding and/or hurricanes. Mold may result from ongoing water leakage and/or other structural issues. In many cases, mold grows inside the walls and/or ceiling of a building. This presents a challenge in detecting and assessing the extent of mold. In some cases, the wall, ceiling, and/or floor is opened up to determine the presence or absence of mold. However, creating access points to check for mold and/or assess the extent of mold may result in damage that then needs to be repaired.

BRIEF DESCRIPTION OF THE DRAWINGS

The accompanying drawings illustrate various examples of the principles described herein and are a part of the specification. The illustrated examples do not limit the scope of the claims.

Throughout the drawings, identical reference numbers designate similar, but not necessarily identical, elements. The figures are not necessarily to scale, and the size of some parts may be exaggerated or minimized to more clearly illustrate the example shown. The drawings provide examples and/or implementations consistent with the description. However, the description is not limited to the examples and/or implementations shown in the drawings.

DETAILED DESCRIPTION

It may be desirable to detect and characterize the extent of mold behind a surface without putting holes in the surface covering the mold. This allows formation of a plan to treat the mold without opening up the space and releasing spores into the environment. In some cases, the size of the mold-covered area will impact the treatment/remediation approach taken.

Among other examples, this specification describes a method of determining an extent of mold behind a surface. The method includes moving a gas sensor lateral to the surface. The method also includes measuring gas concentrations at multiple points along the surface.

The present specification also describes a system for mapping gas concentrations at a surface. The system includes a drone with a gas sensor and a transmitter. The system also includes a receiver in communication with the drone. The receiver receives transmissions from the drone which include gas measurements, and distances between the gas sensor and the surface.

This specification also describes a method for determining an extent of mold behind a wall. The method includes taking gas concentration measurements at multiple points near the wall using a drone-mounted gas sensor. The method also includes displaying a mapping of the gas concentration measurements, which measurements indicate a presence of mold behind the wall.

Figure 1:
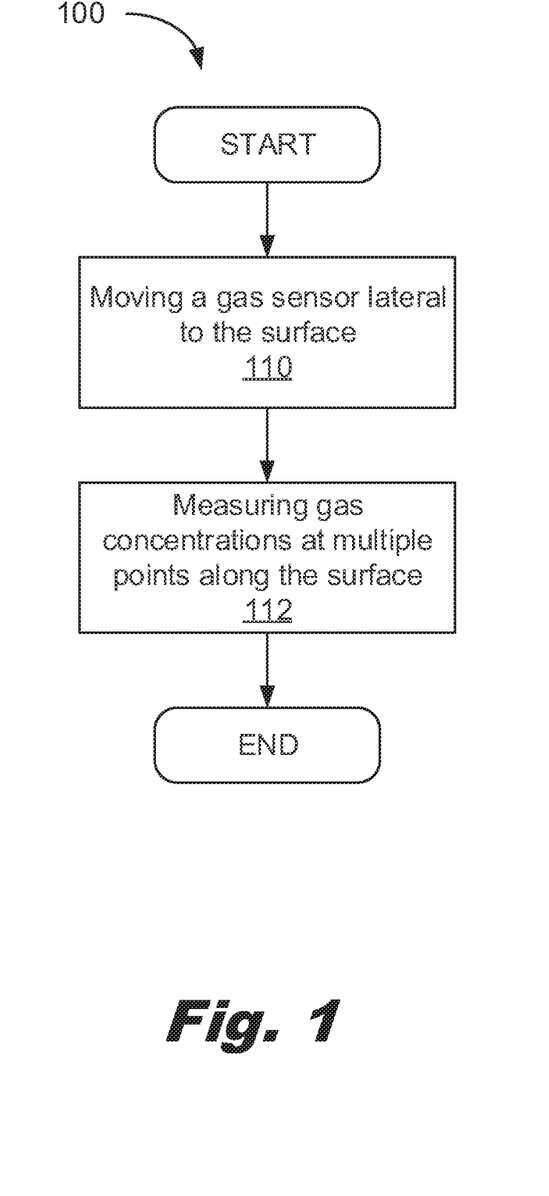
FIG. 1 shows a flowchart for a method of identifying mold behind a surface according to an example consistent with the present specification.

Turning now to the figures, FIG. 1 shows a flowchart for a method (100) of determining an extent of mold behind a surface, according to an example consistent with the present specification. The method (100) includes 1) moving (110) a gas sensor lateral to the surface and 2) measuring (112) gas concentrations at multiple points along the surface.

The method (100) relies on the observation that mold, when present behind a surface, distorts the gas concentrations at the surface. That is, the mold may produce gases which are detectable. In some examples, the gases may be relatively rare in the atmosphere such as Microbial Volatile Organic Compounds (mVOCs). These mVOCs can include a variety of organic species including hydrocarbons, benzene derivatives, etc. In another example, the gases may be relatively common in the atmosphere, e.g., water, carbon dioxide, and/or oxygen.

When mold is present, the local level of carbon dioxide may be 10× to 1000× higher than atmospheric levels, which atmospheric levels may be 0.04% or about 400 parts-per-million (ppm). Additionally, oxygen may be depleted in the presence of mold (each depleted oxygen molecule providing a pair of oxygen molecules in the emitted carbon dioxide). However, as oxygen is 20.95% of the atmosphere, this is a much smaller relative change. Moisture may be an indicator of a mold problem or a potential mold problem. Accordingly, measurements of these gases may be assessed on a basis relative to measurements on other portions of the surface. The measurements on these other portions provide a useful baseline, especially for variation in humidity.

The method (100) may treat the mold as a set of point sources. That is, a point source of a gas under pure diffusion in a uniform medium without convection has a concentration drop as a function of the square of the radius. This is due to the spread of an amount of gas over increasingly larger volumes as the gas diffuses outward. In another example, an area of uniform concentration of mold may be modeled as a planar generator with a uniform near field concentration. Accordingly, the methods of modeling gaseous diffusion in the absence of convection for both homogeneous and heterogeneous environments may follow mass transfer principles.

The method (100) includes moving (110) a gas sensor lateral to the surface. In some examples, the gas sensor contacts the surface and in other examples, the gas sensor is separated from the surface by a gap. The gas sensor may have an associated standoff device, for example, a wheel, skid, fin, rail, etc. to provide a fixed spacing between the surface and the gas sensor. Moving the gas sensor lateral to the surface allows mapping of the target gas concentration with respect to the surface, allowing assessment of the extent of mold behind the surface.

The method (100) includes measuring (112) gas concentrations at multiple points along the surface. In some examples, the points are part of a predetermined pattern. For example, the points may form a grid having a first spacing. Once the grid is complete and a mold region identified, intermediate points and/or extrapolated points may be added to further define the perimeter of the mold region. In another example, the points are generated procedurally based on the accumulated previous measurements. This may reduce time measuring the interior of a mold region. In another example, a user selects a point and/or point patterns from a display and/or similar interface as data is being accumulated. In such an approach, the user may dynamically adjust the sampling patterns to minimize time and maximize operation. In some examples, the user may allow a predetermined pattern to be run. The interface may provide the user with recommendations for additional measurements, either while the pattern is being run and/or after the pattern is completed. In some examples, the interface may provide recommended sampling patters prior to beginning measurements. In some examples, additional measurements may replicate measurement locations. That is, the additional sampling may include measurements taken at the same lateral position relative to the surface but with a different standoff (separation from the surface).

In some examples, the gas concentration that is measured (112) may be carbon dioxide concentration, water vapor concentration, and/or other gas concentration.

The gas sensor may include a first oscillator which oscillates at a high (MHz) frequency at the measurement point. Changes in mass to the first oscillator impact the frequency of oscillation. For example, the addition of mass to the first oscillator may increase the period and decrease the frequency. Decreases in mass of the surface of the oscillator, for example from desorption of gas from the surface, may decrease the period and increase the frequency of oscillation. Accordingly, the first oscillator has a first surface which oscillates. That is to say, the first surface is not a fixed part of the first oscillator but rather is associated with a moving portion of the first oscillator. This first surface supports reversible adsorption of a gas.

In some examples, the system may use quartz crystal microbalance ("QCM") sensors for the first oscillator. In other examples, the first oscillator may be a Capacitive Micromachined Ultrasound Transceivers ("CMUTs"), a Piezoelectric Micromachined Ultrasound Transceivers ("PMUTs") and/or a Microelectromechanical System ("MEMS"). In yet other examples, the system may be implemented as a Tow Tomas oscillator, a Sullen and Key configuration, a Colpitts oscillator, Clapp oscillator and/or other variations. The oscillators in these devices operate at high frequencies and accordingly draw power in several milliamps ("mA") to tens of mA. The high frequency used is a component of high-power dissipation associated with these types of oscillators as sensors.

In some examples, the first surface of the first oscillator may be modified to increase the adsorption of a gas. For example, the first surface may be oxidized, coated, textured, and/or otherwise modified. In an example, the first surface is a material deposited on a substrate of the first oscillator. For example, the first surface may be a metalized layer on a piezoelectric substrate of the first oscillator. The first surface may also function as an electrode for the first oscillator. For example, the first surface may be deposited on and/or formed from a metalizing layer on a surface of the first oscillator. In yet another example, the first surface may be a coating. As a specific example, the first surface is a functionalized coating selected to interact with carbon dioxide.

One way to use crystal-based and/or other oscillators is to extract measurements and perform a regression to identify the frequency of the oscillator. For example, voltage/time information could be processed using a Fast Fourier Transform (FFT). Other similar matrix-based techniques may be used. These approaches provide the ability to make determinations about oscillating frequency and to identify noise sources and contributions. This additional information may be useful in other applications, such as ultrasonic imaging. However, these approaches are also processor and power intensive. Performing such calculations in real-time for a system places additional demands on the supporting processor(s)/logics. This additional processing capacity increases costs and power consumption.

Another approach is to use a first counter to count oscillations of the first oscillator. If the variable being evaluated is the frequency shift of the first oscillator, then performing additional computations to regress the frequency using a transform and/or similar computational intensive method is surplus and wasteful. Instead, a first counter accumulates cycles of the first oscillator. In some examples, the first counter may include a reset line. The first counter may trigger using a condition selected from a range of different conditions, including passing a zero value, peak, valley, high-low transition, low-high transition, etc. While the logics of the first counter may operate at the expected frequency of the first oscillator, e.g., 10,000 Hz but less than 300,000,000 Hz, the rest of the system may be operated at a lower frequency. In an example, the frequency of the first oscillator is between 20 MHz and 100 MHz. More specifically, the frequency of the first oscillator may be between 60 MHz and 90 MHz. Operating at a lower frequency reduces the power consumption.

In general, the gas concentration being monitored is a slow moving signal. Accordingly, sampling the signal on a sub 100 Hz basis does not make the information less timely and/or accurate. Indeed, averaging the signal over a longer time provides stability benefits to the measured values. Accordingly, performing gas concentration sampling and calculation at the lower frequency reduces power consumption without reducing the sensitivity to the gas concentration being monitored. This approach works for one type of gas sensor with sensitivity, low power consumption, and low processor demands (on the sensor/drone/robot). However, the disclosed method may work with a wide variety of gas sensors.

The method (100) may further include measuring a distance to the surface from the gas sensor using an ultrasound sensor. In some examples, gas concentration measurements are taken at various distances to enhance the estimate of the extent and uniformity of the mold behind the surface. For example, if the concentration drop resembles a radius^2 decrease, the shape of the mold resembles a point source. Similarly, if the concentration drop is slow, then the shape of the mold may be inferred to resemble a plane and/or similar source shape. The rate of concentration drop with respect to a distance away from the surface may also increase edge detection. This is because at the edge of mold, the behavior of a planar source transitions from constant to first order with respect to radius (standoff).

In some examples, the method (100) includes taking measurements at points having a first separation, and then making measurements at points having a second, and smaller, separation to refine the boundaries of a region of gas concentration perturbation from a local mean concentration. This process may be performed iteratively to provide increasing resolution of the boundaries. In other examples, such iterative measurements may also be used to identify studs, pipes, and other obstructions in the wall which may produce small local gas deviations. Identifying such features may facilitate forming a remediation plan and/or avoiding accidental damage to pipes, wires, etc.

The method (100) may further include mapping the gas concentration measurements to identify regions of the surface having a deviation in gas concentration associated with mold behind the surface. The map may be a heat map of the gas concentration measurements. In some examples, the map includes interpolations between measured points. In some examples, the map is overlaid on an image of the surface. Such an image may include a reference point put on the surface, for example, a sticker and/or similar marker. The image may use reference points on the surface, for example a window frame, a bookshelf, etc.

In an example, the gas sensor is mounted on a drone. The drone may be preprogrammed to fly a course along the surface and/or the drone may be manually controlled. The drone may be programmed to raster across the surface. In some examples, the drone stops at measurement points for a period of time to allow a measurement to be taken. In other examples, the drone moves continuously and the measurement is associated with a point in the motion. In some examples, the drone may raster laterally and/or vertically. In other examples, the drone may raster diagonally, for example at roughly a 45 degree angle relative to a side of the surface, e.g., the floor and/or ceiling.

In another example, the gas sensor may be mounted to a robot. For example, the gas sensor may be mounted on a vertical extension arm. The robot may also include treads, wheels, and/or similar devices to move laterally along a wall. In an example, the robot includes a wheel to run along a baseboard. The robot may be biased so as to move slightly toward the baseboard as the robot moves laterally to the wall to keep the distance between the sensor and the surface (wall) constant. The robot may include a third axis allowing motion relative in the axis orthogonal to the wall. In an example, this third axis data is instead provided by having multiple sensors. Similarly, the robot (or drone) may include an array of sensors allowing measurement of multiple points simultaneously.

In another example, the gas sensor is part of a hand-held device. Such a hand-held device may include a roller ball (like a mouse ball) allowing tracking of motion of the hand-held device along the wall. As the hand-held device is rolled along the wall, the position is tracked by the hand-held device using the roller ball. The gas sensor takes gas sample measurements. In this design, a user activates the hand-held device and places the hand-held device at a start point and then manually moves the hand-held device along the wall until the desired data is acquired. In an example, the hand-held device includes a screen. In another example, the hand-held device couples wirelessly, e.g., Bluetooth®, and/or by port, e.g. Universal Serial Bus-Type C port (USB-C) to a phone, tablet, and/or similar screened computing device, allowing display during use. In some examples, the computing device provides processing power for the analysis. In some examples, the computing device may offload the data analysis to a remote resource, such as a server to perform processor-intensive functions.

The active provision of data to the user may allow the user to concentrate on edges and areas of interest that appear as the data is being generated. The hand-held device may include additional rollers, wheels, skids, etc. to help keep the device flush to the surface.

The method (100) may further include wirelessly communicating the measured gas concentrations to a processor external to a gas sensor. For example, this processor may be in a receiver. This processor may be in a phone, tablet, laptop, desktop, and/or similar computing device. In an example, the sensor communicates via Bluetooth® with a phone. The phone may include a downloadable application (app) to process and/or display the data.

The method (100) may further include wirelessly communicating to a processor external to the drone, robot, or hand-held device or other computing device, a distance between the surface and the gas sensor. The distance may be determined using ultrasound pulse return time as discussed with respect to FIG. 5, below. In other examples, the distance may be determined using another non-contact measurement method, for example, a light-based system. The distance may be determined by determining a location of a drone, device, and/or robot in three dimensions and registering a surface location. In some examples, the method may include calculating a position of the gas sensor relative to a reference point. As described above, the reference point may be associated with the receiver and/or a controller. The reference point may be a marker and/or device placed on the surface. In an example, the reference point includes multiple transponders placed against the surface, for example, at a predetermined spacing. For example, three or more transponders could be in fixed relation to each other, for example, in a plastic overmold. The overmold may include vertical and/or horizontal level bubbles to aid in providing a predetermined orientation for the transponders. The overmold may include an adhesive pad, suction cup, and/or other similar element to reversibly and non-destructively attach the overmold to the surface.

The method (100) may include displaying the gas concentrations in a display. The gas concentrations may be displayed as a heat map. In some examples, the heat map may include interpolations between measured points to generate an estimate of unmeasured areas. The method (100) may include interpolating gas concentrations between measured points and displaying the gas concentrations as a graph in a display. In an example, the heat map includes identification of measured points. The heat map may include indicators of planned points to be measured. The heat map may be limited to interpolations between measured points without extrapolation beyond the measured points. The heat map may allow limited extrapolation, for example, up to 20, 10, 5, 2, and/or some other distance in centimeters or some other value based on predetermined profiles. For example, detection of a greater deviation from an average value in the measured gas may allow greater extrapolation from the measured point, while lower deviation, indicating perhaps less mold and/or approaching an edge, may justify a smaller extrapolation from the measured point. In some examples, no interpolations are used and just areas around the measured point based on the value of the gas measurement.

Figure 2:
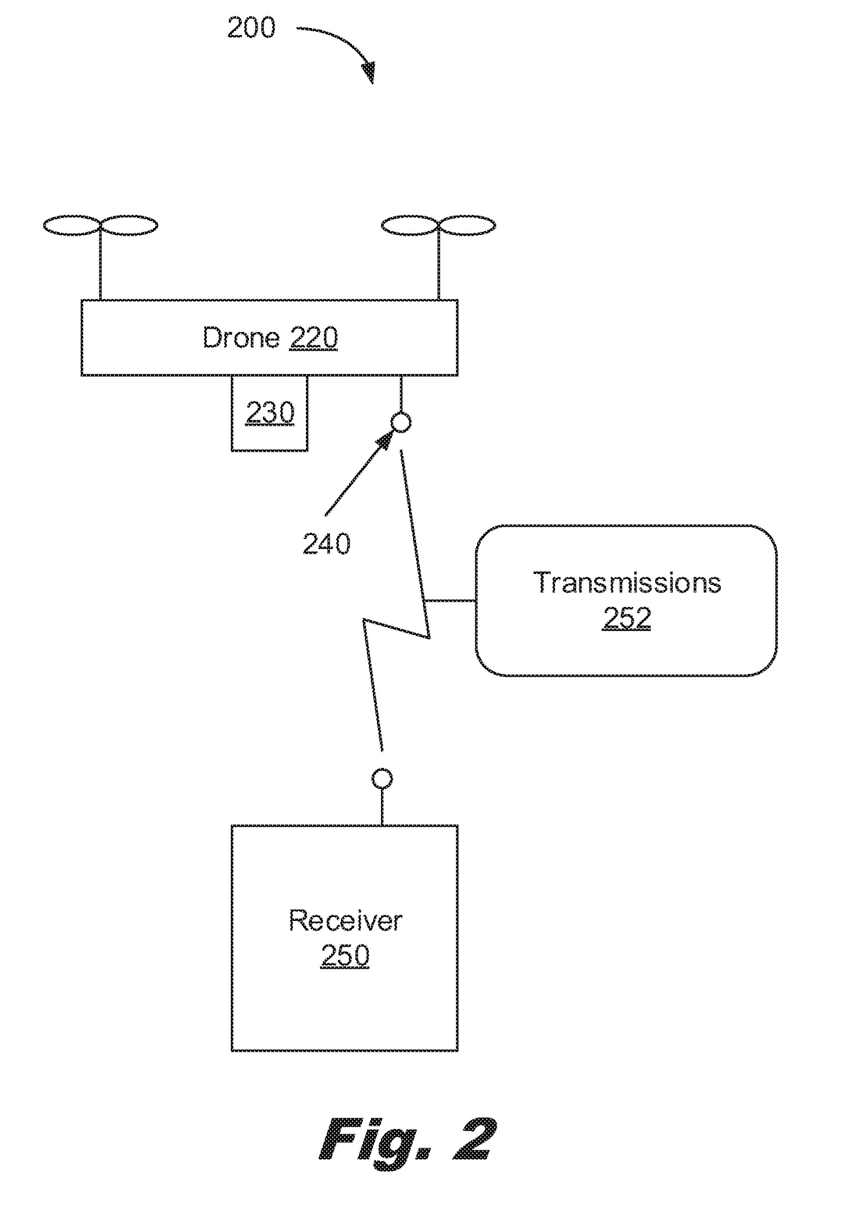
FIG. 2 shows a system for mapping gas concentrations at a surface according to an example consistent with the present specification.

FIG. 2 shows a system (200) for mapping gas concentrations at a surface. The system includes: a drone (220) having a gas sensor (230) and a transmitter (240). The system also includes a receiver (250) in communication with the drone (220), the receiver (250) to receive transmissions (252) from the drone (220). Such transmissions (252) include, gas measurements and distances between the gas sensor (230) and the surface.

The drone (220) carries a gas sensor (230) and in some cases includes a proximity sensor and/or other sensor to detect a distance between the drone (220) and a surface being measured. In some examples, information from the gas sensor (230) and the distance information are transmitted to a receiver (250). In other examples, the information is processed on the drone (220). In some examples, the information is processed by a processor with access to the receiver (250). In some examples, the information is partially processed on the drone (220) and further processing is conducted after the information is received by the receiver (250).

In some examples, the drone (220) may be modified to support a separate gas sensor (230). In other examples, the drone (220) may be a custom drone (220) with the gas sensor (230) integrated into the other systems of the drone (220). This may allow sharing of control signals/bands, power systems, etc. This may in turn reduce the load on the drone (220) and increase flight time.

The gas sensor (230) may be any of a variety of gas sensors (230). The system (200) benefits from a gas sensor (230) with low weight, high stability, low power consumption, and other features. While particular examples of gas sensors (230) are described below, the claims are not limited to these descriptions except to the extent the features are recited in the claims.

The gas sensor (230) may be a gas absorption sensor. Such a gas absorption sensor (230) may include a control oscillator without a gas selective coating. The coating is selected to allow passage and/or absorption of a particular gas. In some examples, the gas sensor (230) may include multiple measurement surfaces with different gas selective coatings. For example, the gas sensor (230) may include a first measurement portion with a carbon dioxide selective absorbing surface and a second measurement portion with a water selective absorbing surface. The sensor systems described in Applicant's U.S. application Ser. No. 15/750,448 are particularly useful for the present application due to their power consumption, sensitivity, reliability, and data transmission efficiency.

In some examples, there is an accelerometer associated with the gas sensor (230). This may allow detection of vibration and/or other noise which makes the sensor less reliable. The system (200) may block such vibration and noise measurements from transmission. In one particular example, the system (200) may flag and/or scrub such measurements after they are received by the receiver (250). In some examples, the system (200) automatically adds a replacement measurement for measurements so flagged and/or blocked.

The system (200) may include an ultrasound distance sensor. The ultrasound distance sensor generates an ultrasound pulse and then detects the first return pulse (while excluding any associated with the drone/sensors/etc.) If the pulse is non-directional, the first return pulse will be from the point orthogonal to the nearest point on the surface. This return pulse will also be stronger than other pulses deflecting off the nearest surface because the pulse will bounce directly back. In contrast, other portions of the surface will deflect the reflected pulse away from the emitting sensor. These geometric relationships strengthen the first return pulse as compared with other return signals from a flat surface.

When the first return pulse is received, the travel time is calculated. The travel time for the pulse is divided by the speed of sound and halved (for there and back) to calculate the distance from the pulse generator/detector to the nearest surface. In some examples, a speed of sound is measured and/or calculated. For example, the system (200) may include two pulse generators/detectors at a fixed distance from each other. A pulse from the first generator could be detected at the second sensor to assess the speed of sound. This may be the same pulse used to assess the distance to the surface. In other example, the speed of sound is represented by a constant. In some examples, a correction is added for a displacement between the gas sensor (230) and the pulse generator/detector.

The transmitter (240) may be located separate from the gas sensor (230). The transmitter (240) provides data transmission to the receiver (250). The data transmissions (252) include at least the gas concentration data and the distance data. In some examples, the data may be processed in part and/or completely on the drone (220) while in other examples, the data may be transmitted in an unprocessed form. There is a tradeoff between transmission bandwidth and processing power on the drone, with the associated weight and power to support the processing power.

The receiver (250) maybe associated with a processor. The receiver (250) receives the transmissions (252) including the gas concentration data and distance data.

The transmissions (252) may be organized in any useful format. A given transmission (252) may contain gas concentration data, distance data, other data, and/or combinations of the above. For example, the gas concentration data may be transmitted every 100 milliseconds. The distance data transmitted every 250 milliseconds. Each gas concentration data point may be transmitted with an associated distance data.

Figure 3:
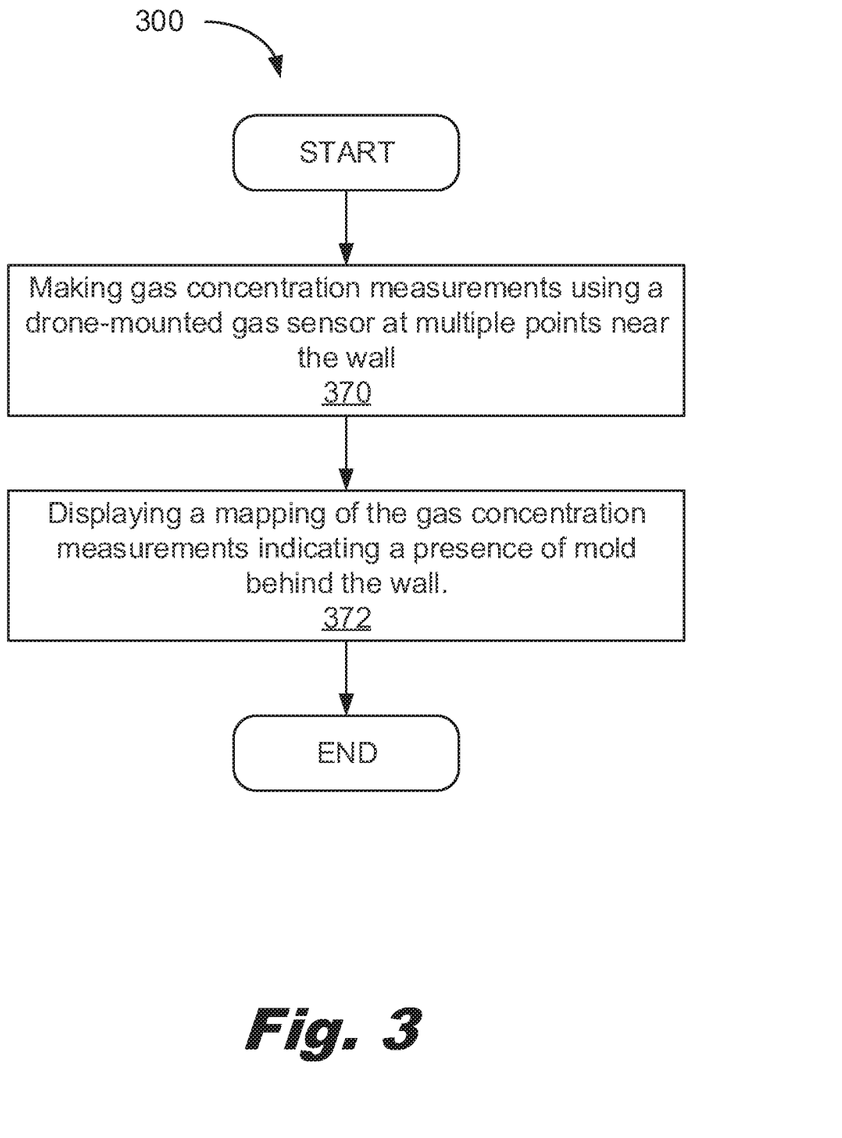
FIG. 3 shows a flowchart for a method of identifying mold behind a surface according to an example consistent with the present specification.

FIG. 3 shows a flowchart for a method (300) of determining an extent of mold behind a wall, according to an example consistent with the present specification. The method (300) includes 1) making (370) gas concentration measurements using a drone (220) mounted gas sensor (230) at multiple points near the wall and 2) displaying (372) a mapping of the gas concentration measurements indicating a presence of mold behind the wall.

The method (300) allows a drone (220) mounted gas sensor (230) to acquire gas concentration measurements and then display those measurements to assess the extent of mold behind the wall. This may be performed without breaching and/or otherwise opening the wall. That is, drilling holes into the wall or otherwise creating access points which need repair may be avoided.

In some examples, the gas concentration measurements include carbon dioxide measurements. In other examples, the gas concentration measurements may include water vapor measurements.

The method (300) may further include measuring a distance between the wall and the gas sensor (230) for each gas concentration measurement. This may be done using an ultrasound sensor. Any gas concentration measurement is then adjusted based on an associated, measured distance. One advantage of using the ultrasound sensor as both a distance sensor and the gas sensor is the lack of offset between the two sensor locations which might otherwise need to be accounted for.

Figure 4:
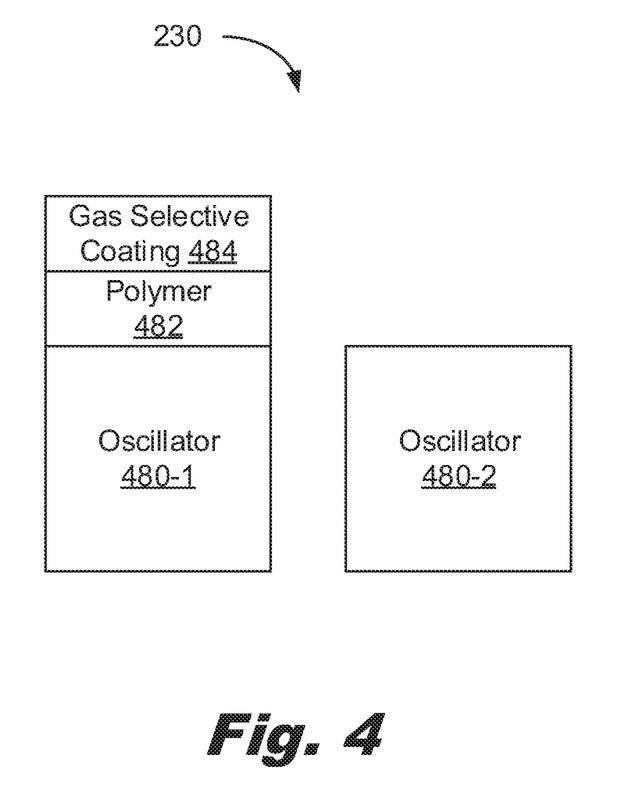
FIG. 4 shows an example of a gas sensor for detecting mold consistent with the present specification.

FIG. 4 shows an example of a gas sensor (230) for detecting mold consistent with the present specification. The gas sensor (230) includes a pair of oscillators (480-1,-2) each of which has an associated polymer coating (482). One of the oscillators (480-1) further has a gas selective coating (484) on top of the polymer (482-1). The gas selective coating (484) provides the desired selectivity for the gas sensor (230).

Counts of the oscillators (480) may be recorded and a difference in counts between the two oscillators (480) used to determine a gas concentration. The data may be output as counts, difference in counts, counts per unit time, and/or other formats. The use of efficient output formats may also reduce the power requirements for the drone (220) and/or gas sensor (230) system. For detail is available in Applicant's previously filed U.S. Ser. No. 15/750,448 Application, which fully describes the details of a gas sensor and its use. That application is incorporated by reference herein.

Figure 5:
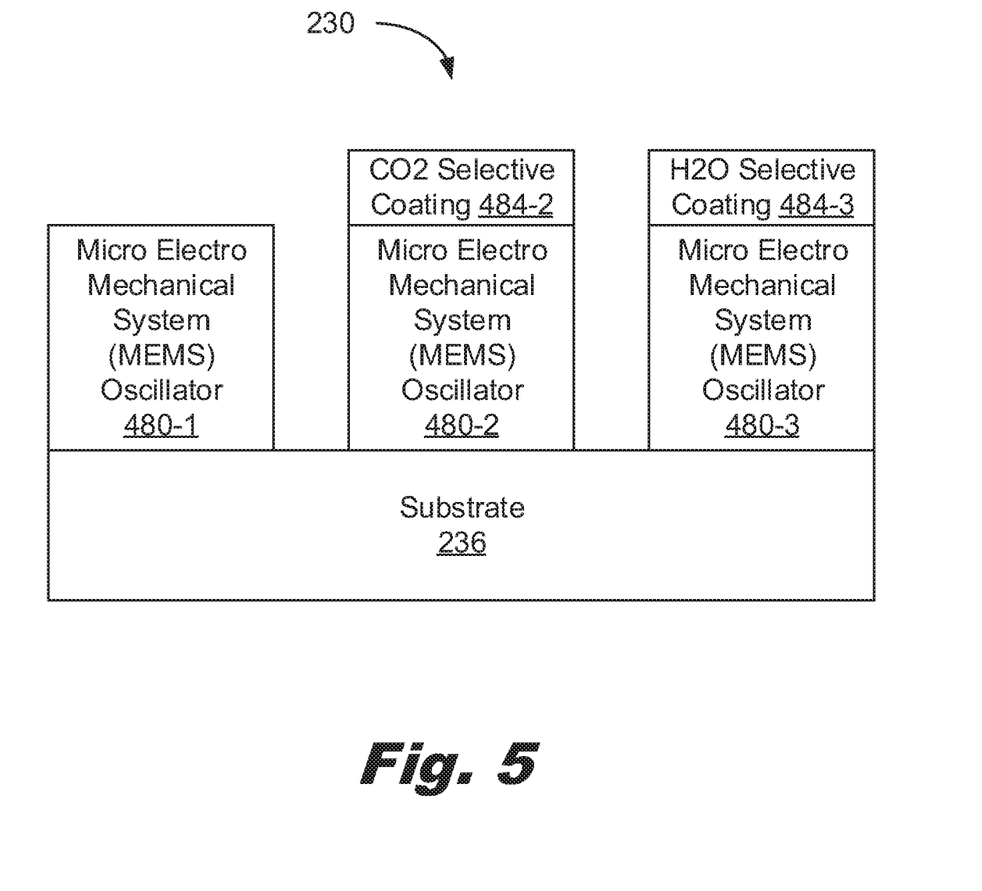
FIG. 5 shows an example of a gas sensor for detecting mold consistent with the present specification.

FIG. 5 shows an example of a gas sensor (230) for detecting mold consistent with the present specification. The gas sensor (230) includes three (or more) oscillators (480), specifically Micro Electro Mechanical Systems (MEMS) oscillators, on a substrate (236) each of which has an associated polymer coating (482). Two of the oscillators (480-2 and 480-3) further have gas selective coatings (484-2, -3) on top of the polymer (482). The gas selective coatings (484-2,-3) provides carbon dioxide and water selectivity respectively.

Figure 6:
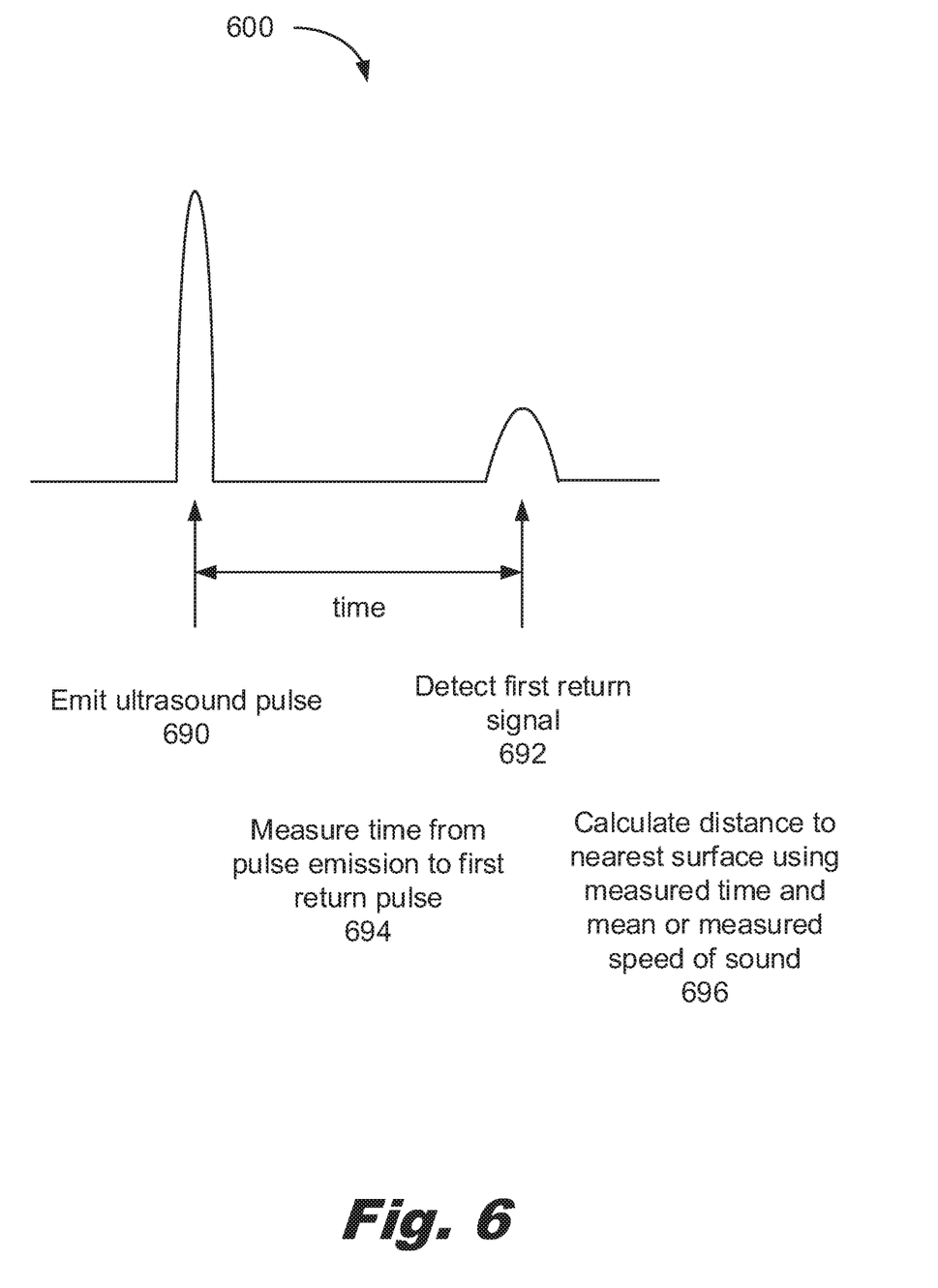
FIG. 6 shows an example of surface distance detection consistent with the present specification.

FIG. 6 shows an example of surface distance detection consistent with the present specification. An ultrasound source generates an ultrasound pulse (690). That ultrasound pulse (690) travels until the pulse reflects off a nearest surface and returns to the ultrasound source. The ultrasound source then detects the first return signal (692). The time between emission of the pulse and the first return pulse is measured (694). The distance between the ultrasound source and nearest surface is then calculated using the measured time and the speed of sound (696).

The ultrasound source may serve as both 1) the distance sensor and 2) the gas sensor (230). This provides a "free" distance sensor on the already compact and lightweight gas sensor (230). The integration of both sensors provides advantages in reducing parts and weight on the drone (220). This may also reduce the total power requirements for the gas sensor (230) combination with a distance sensor. However, this integration of the two sensors (gas and distances) while useful is not required for the described methods and devices. Instead, it provides additional benefits over the use of separate sensors.

More complex methods using multiple ultrasounds sources and/or detectors may be used to provide redundancy, evaluate rotation of the gas sensor; control for the speed of sound, etc. may be readily envisioned. Other methods of measuring the standoff from a surface may be used including light interference methods.

It will be appreciated that, within the principles described by this specification, a vast number of variations exist. It should also be appreciated that the examples described are only examples, and are not intended to limit the scope, applicability, or construction of the claims in any way.

What is claimed is:

1. A method of determining an extent of mold behind a surface, the method comprising:
   moving a gas sensor lateral to the surface, the gas sensor comprising an oscillating gas-interacting surface;
   measuring gas concentrations at multiple points along the surface; and
   displaying a heatmap in a display, the heatmap showing the measured gas concentrations at multiple points along the surface.

2. The method of claim 1, wherein measuring gas concentrations comprises measuring carbon dioxide concentrations.

3. The method of claim 1, wherein measuring gas concentrations comprises measuring water vapor concentrations.

4. The method of claim 1, wherein the gas sensor is mounted on a drone.

5. The method of claim 4, further comprising measuring a distance between the surface and the gas sensor using an ultrasound sensor of the drone.

6. The method of claim 1, further comprising mapping the gas concentrations to the multiple points to identify regions of the surface having a deviation from a baseline gas concentration, which deviations are associated with mold behind the surface.

7. The method of claim 1, wherein measuring gas concentrations at multiple points along the surface comprises:
   making measurements at points having a first separation distance from the gas sensor; and making measurements at points having a second, and smaller, separation from the gas sensor to refine boundaries of a region of gas concentration perturbation from a local mean concentration.

8. The method of claim 1, further comprising wirelessly communicating the measured gas concentrations to a processor external to the gas sensor.

9. The method of claim 8, further comprising wirelessly communicating, to a processor external to a drone on which the gas sensor is located, the separation distance between the surface and the gas sensor.

10. The method of claim 9, further comprising calculating a lateral position of the gas sensor relative to a reference point on the surface.

11. The method of claim 8, further comprising interpolating gas concentrations between measured points and displaying the gas concentrations as a graph in a display.

12. The method of claim 1, further comprising
   displaying a mapping of the gas concentration measurements, which measurements indicate a presence of mold behind the surface.

13. The method of claim 12, wherein the gas concentration measurements comprise carbon dioxide measurements.

14. The method of claim 12, further comprising:
   measuring a distance from the surface for each gas concentration measurement; and
   adjusting the gas concentration measurement based on an associated distance to the surface.

* * * * *